United States Patent [19]

Glowczewskie, Jr. et al.

[11] Patent Number: 4,844,259
[45] Date of Patent: Jul. 4, 1989

[54] MEDICAL AND SURGICAL PROCEDURE PACK

[75] Inventors: Frank P. Glowczewskie, Jr., Gainesville, Fla.; David A. Present, New York, N.Y.

[73] Assignee: Osteotech, Inc., Shrewsbury, N.J.

[21] Appl. No.: 136,408

[22] Filed: Dec. 22, 1987

[51] Int. Cl.⁴ .................. B65D 83/10; A61B 17/06
[52] U.S. Cl. .................. 206/370; 206/439; 206/440
[58] Field of Search ............ 128/132 D; 206/370, 206/438, 439, 440, 571, 572, 613

[56] References Cited

U.S. PATENT DOCUMENTS

| | | | |
|---|---|---|---|
| 1,434,566 | 11/1922 | Sharp | 206/440 |
| 2,947,415 | 8/1960 | Garth | 206/364 |
| 3,362,617 | 1/1968 | Gieber | 206/613 |
| 3,770,119 | 11/1973 | Hultberg et al. | 206/439 |
| 3,797,652 | 3/1974 | Chesky | 206/438 |
| 3,802,555 | 4/1974 | Grasty et al. | 206/438 |
| 3,851,649 | 12/1974 | Villari | 206/571 |
| 3,926,309 | 12/1975 | Center | 206/364 |
| 3,954,174 | 5/1976 | Kraus | 206/572 |
| 4,042,170 | 8/1977 | Ekman et al. | 206/439 |
| 4,149,635 | 4/1979 | Stevens | 206/370 |
| 4,153,160 | 5/1979 | Leigh | 206/370 |
| 4,175,659 | 11/1979 | Horian et al. | 206/223 |
| 4,437,568 | 3/1984 | Hamblin | 206/223 |
| 4,523,679 | 6/1985 | Piakoff et al. | 206/439 |
| 4,700,838 | 10/1987 | Falciani et al. | 206/438 |
| 4,714,595 | 12/1987 | Anthony et al. | 206/439 |

Primary Examiner—Richard J. Johnson
Assistant Examiner—Lynda M. Cofsky
Attorney, Agent, or Firm—Dilworth & Barrese

[57] ABSTRACT

Medical and surgical procedure packs for carrying out the surgical removal of bone and connective tissue and packaging means for storing and transporting said bone and connective tissue.

7 Claims, 9 Drawing Sheets

MEDICAL AND SURGICAL PROCEDURE PACK

BACKGROUND OF THE INVENTION

This invention relates to the sterile packaging of components useful in certain medical and surgical operative procedures and more particularly to pre-sterilized packs containing pre-sterilized medical and surgical items needed to perform medical and surgical procedures in connection with the sterile recovery of bone and connective tissue.

While the concept of the present invention is applicable to the prepackaging of any medical and/or surgical items required for any routine medical and/or surgical procedure, the packages provided by the present invention are particularly suited for procedures employed in the recovery of muscular skeletal tissue from human cadavers for the purpose of subsequent transplant. Generally, such procedures involve the steps of preparing the donor involving, inter alia, scrubbing of and removal of all body hair from the donor, followed by sterile draping of the donor and the surgical removal of bone and connective tissue. Finally, removed skeletal tissue is sterilely packaged for transport and storage.

Each of the aforedescribed steps requires the utilization of certain items to carry out the particular procedure. In the past, a surgeon and/or technician or other member of the procurement team performing or assisting at the procedure has not had ready access to all of the items required to carry out the process involved. Such inaccessibility generally makes performing the procedure, particularly under the required sterile conditions, difficult, if not impossible.

SUMMARY OF THE INVENTION

Accordingly, it is one object of the present invention to provide an improved pre-sterilized medical and surgical procedure pack or kit.

It is another object of this invention to provide a pre-sterilized medical and surgical pack or kit containing all the medical and surgical items required for carrying out the various stages in the surgical removal of bone and connective tissue from a donor.

Still another object of the present invention is to provide a pre-sterilized medical and surgical procedure pack or kit, which integrates both all the medical and surgical items used in the surgical procedure of removing bone and connective tissue and all those post-surgical items required to sterilely package the removed bone and connective tissue.

Yet another object of this invention is to provide a novel packaging means and process for packaging and storing the removed bone and connective tissue.

DETAILED DESCRIPTION OF THE INVENTION

The medical and surgical packs or kits of the present invention provide in a single package all the diverse and essential components required for the sterile recovery of bone and connective tissue from a donor cadaver, including those items necessary to prepare the donor, drape the donor, remove the bone and connective tissue and sterilely pack the recovered tissue for subsequent transport and storage.

Thus, in accordance with the present invention, and in one embodiment thereof, a pre-sterilized pack comprised of an inner, pre-sterilized, unit containing all of the items required for the preparation of a donor cadaver prior to the removal of the bone and connective tissue therefrom, contained within an outer package wrap, is provided.

In accordance with another embodiment of the present invention, a pre-sterilized pack comprised of an inner, pre-sterilized, unit containing all of the components required to drape a donor cadaver for the surgical removal of bone and connective tissue therefrom and further to sterilely package the removed bone and connective tissue contained in an outer pre-sterilized wrap, is also provided.

Figures 1, 2:
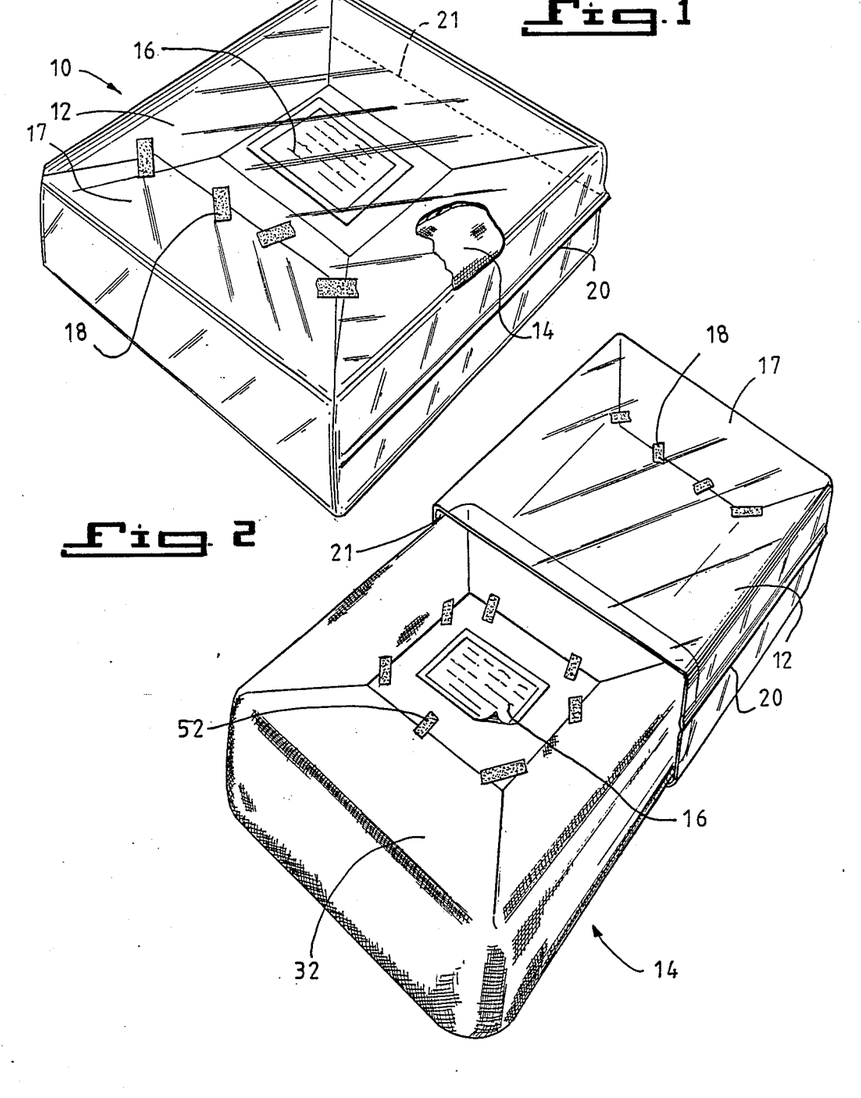
FIG. 1 is a perspective view (partially broken away) of one embodiment of the pre-sterilized pack of the present invention as it would be delivered for subsequent use by a surgeon or technician.
FIG. 2 is a perspective view of the pre-sterilized pack of FIG. 1, illustrating the wrapped inner package unit, as it is taken out of the outer wrap.
Figures 4, 5, 5A:
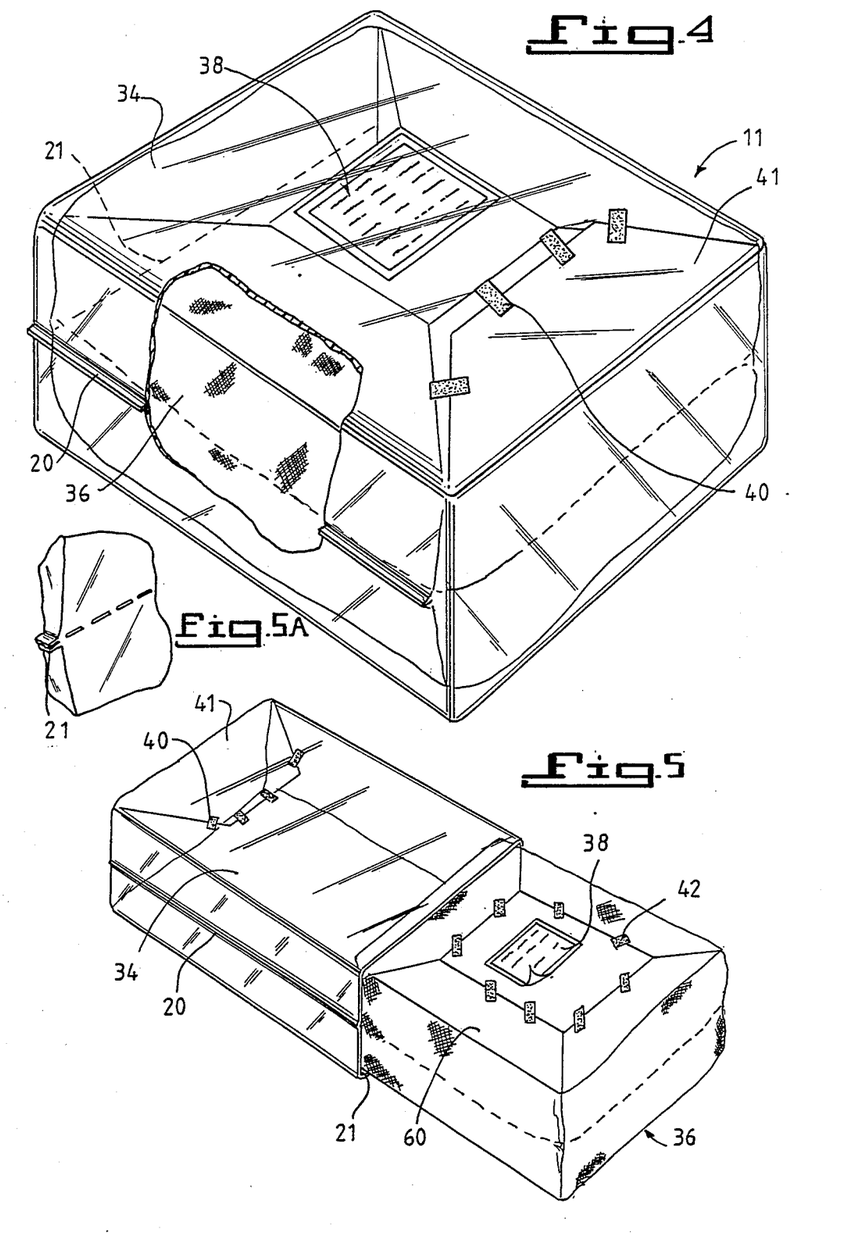
FIG. 4 is a perspective view (partially broken away) of another embodiment of the pre-sterilized pack of the present invention as it would be delivered for subsequent use by a surgeon or technician.
FIG. 5 is a perspective view of the unwrapped inner package unit of FIG. 4, as it is taken out the outer wrap.
FIG. 5A is a corner view of the tear-away side of the outer wrap of FIGS. 1 and 4.

Referring now more particularly to FIG. 1, there is generally provided a medical and surgical pack 10 containing all the items necessary for preparing a donor cadaver for the removal of bone and connective tissue therefrom. The pack 10 is comprised of an outer package wrap constructed of a suitable packaging material, such as a plastic material, for example, polyethylene and the like, sealed around an inner package unit 14, better illustrated by FIG. 2. The outer package wrap 12 may bear printed matter or more preferably is comprised of a clear plastic so that a label 16 of printed matter, indicating, inter alia, the nature of the package contents, may be placed between the outer wrap 12 and the inner wrap unit 14 thereby being visible without unwrapping the pack 10. The outer wrap 12 is preferably constructed from an initially open ended bag, having two pre-sealed sides 20, usually heat sealed, and a third pre-sealed, tear-away closure side 21 (shown in FIG. 1) for the purpose of unwrapping the pack 10, as shown in FIG. 2. FIG. 5A illustrates a corner view of the tear-away closure side 21 of the outer wrap 12. In sealing the inner wrap unit 14 within the outer wrap 12, the initially open end of outer wrap 12 is formed into a flap 17 and the flap 17 is folded back and sealed, for example, by using strips of adhesive tape 18, as illustrated in FIG. 1, or by heat sealing or by any other effective sealing means. In unwrapping the pack 10, flap 17 is left sealed and the tear-away side 21 of outer wrap 12 is torn open.

Inner wrap unit 14, is wrapped with a gas permeable wrapping 32, generally constructed from commercially available regular sterile wrap, such as KIM GUARD, sold by Kimberly-Clark. Sufficient amount of wrapping 32 is provided so that the inner wrap unit 14 can be completely wrapped, as shown in FIG. 2. That is, after container 22 (FIG. 3) and its contents are completely covered by wrapping material 32, the four sides of wrapping 32 are folded back, as shown in FIG. 2, and the four resultant flaps are sealed, for example, by using adhesive strips 52. Upon unwrapping inner wrap unit 14, wrapping material 32 serves as a table cover for placing the items contained in container 22.

Figure 3:
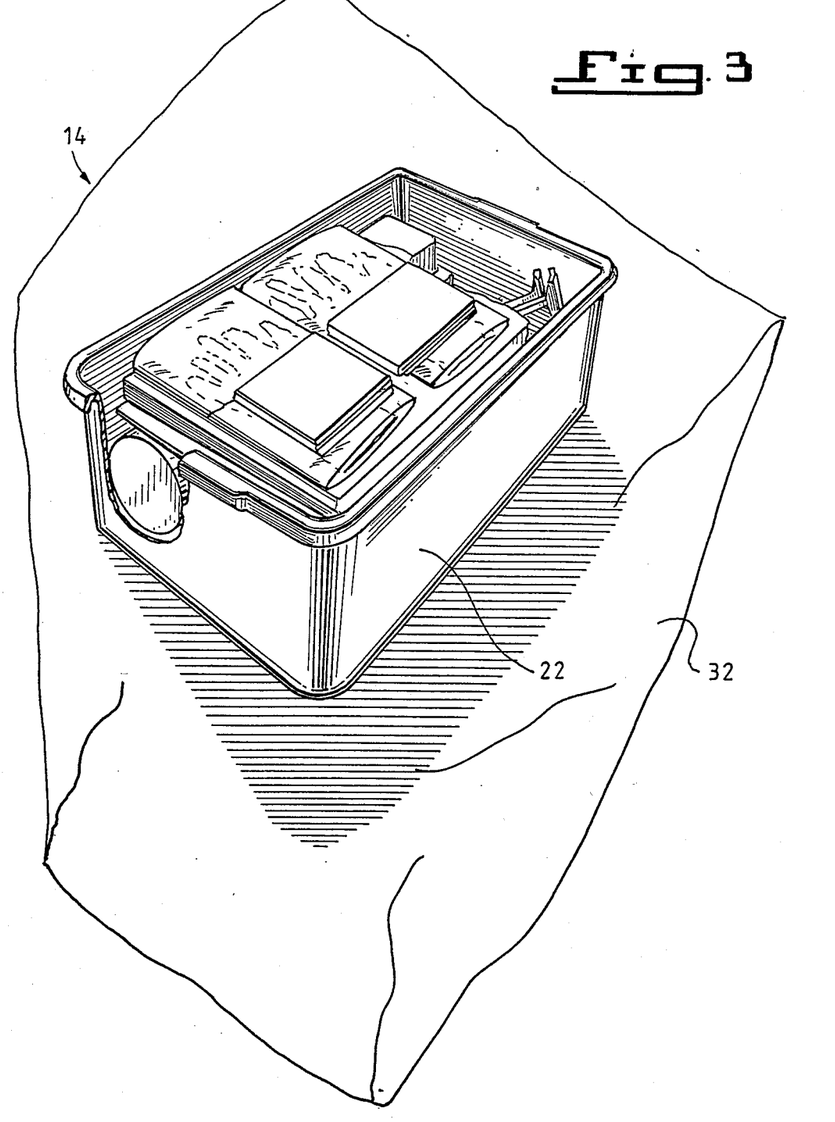
FIG. 3 is a perspective view of the unwrapped inner package unit of FIG. 2, showing some of the items contained therein.
Figure 3A:
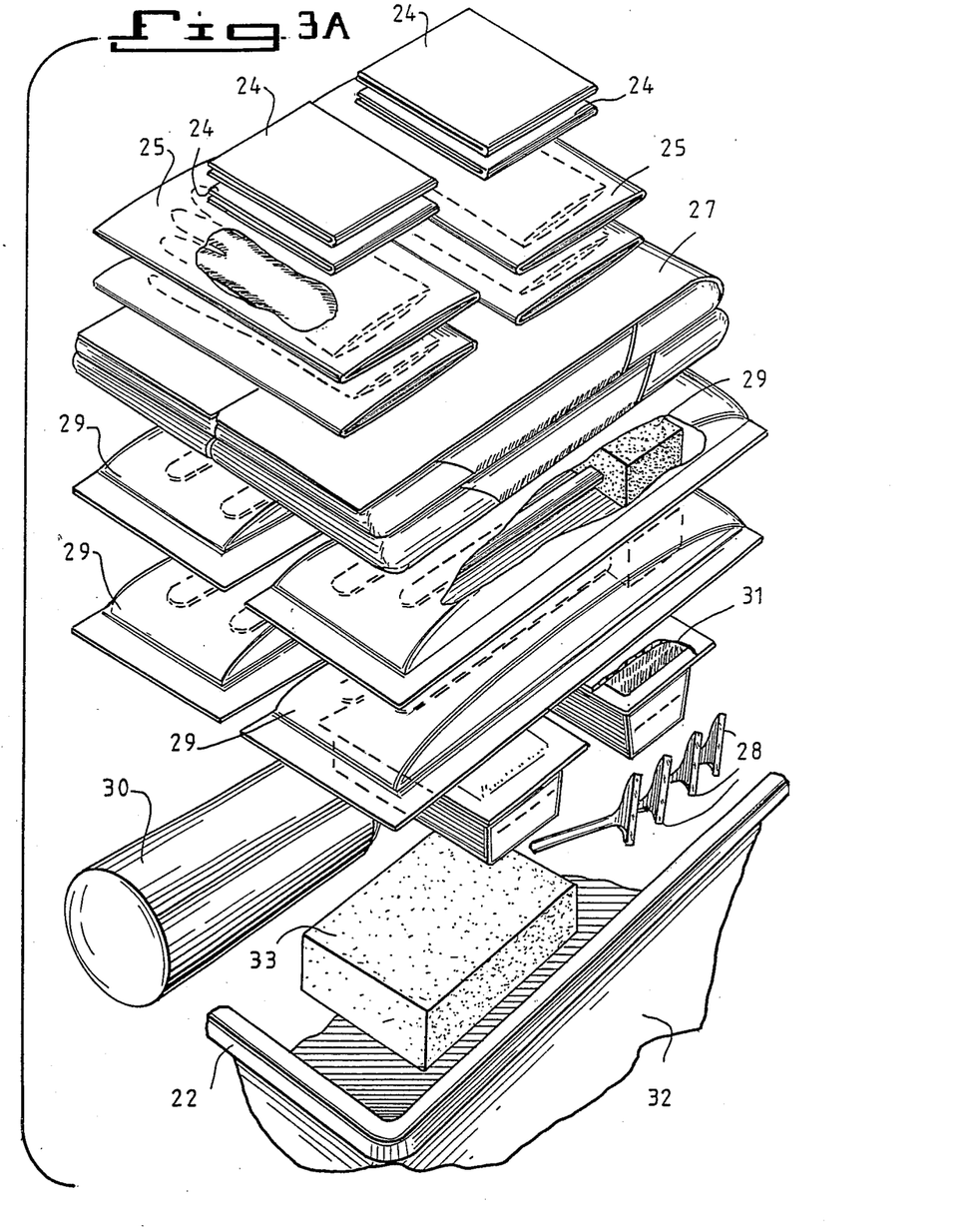
FIG. 3A is an exploded view of FIG. 3 showing the items contained in the inner package unit and the order of arrangement therein.

FIG. 3 illustrates the inner package unit 14 of FIG. 2 in an unwrapped state. As illustrated by FIG. 3, the inner package unit 14 comprises a container 22, which for example, can be a molded or thermo-formed plastic basin, such as an 8 qt. basin, for holding the items to be used in preparing the donor for removal of bone and connective tissue therefrom. More particularly, and as better illustrated by FIG. 3A, those items contained in container 22, which are used to prepare a donor cadaver for the removal of bone and connective tissue, are absorbent towels 24, preferably paper absorbent disposable towels (preferably four), packaged latex gloves 26 (preferably four pair), a folded patient covering means 27, such as a surgical drape, preferably a clear plastic U drape having an adhesive edge on the U portion (preferably four in quantity), cleansing and scrubbing means, such as packaged sponge sticks impregnated with antiseptic 29 (preferably four), scrub brushes impregnated with antiseptic 31 (preferably four in quantity), razors 28, preferably disposable razors (preferably six), a soap sponge 33 (preferably one) and a spray bottle 30, preferably one with a trigger handle for spraying liquid (preferably one).

The order in which the afore-recited items are arranged or placed in container 22, before being sealed in the inner wrapping 32 is essential to the present invention. The items are arranged in container 22 generally in the opposite order in which they are to be used by the technician or surgeon or other assistant carrying out the procedure, thereby providing the technician or surgeon ready access to all the required items, without fumbling and/or loss of sterile conditions.

More particularly, in preparing the embodiment of FIGS. 1 and 2 for use, the container 22 is equipped with the required items in the following order: spray bottle, cleansing sponge, e.g., soap impregnated sponge, razors, scrub brushes, sponge sticks, i.e., antiseptic impregnated sticks, surgical drape, surgeons gloves, absorbent towels.

In the embodiment of FIG. 4, a further medical and surgical pack 11 or kit in accordance with the present invention containing all the items necessary to drape a donor to provide a sterile field, perform the surgical procedure to remove bone and connective tissue from the donor and finally package the removed bone and tissue, is provided.

Thus, referring to FIG. 4, the outer package wrap 34, as with the embodiment of FIGS. 1 and 2, is comprised of a suitable packaging material, such as a plastic material, for example, polyethylene or the like, sealed around an inner package unit 36. The outer package wrap 34 may bear printed matter or more preferably is comprised of a clear plastic so that a label 38, bearing printed matter, may be placed between the outer wrap 34 and the inner wrap unit 36 thereby being visible without unwrapping the package. The outer wrap 34 is preferably constructed from an initially open ended bag, having two pre-sealed sides 20, usually heat sealed and a third pre-sealed, tear-away closure side 21 for the purpose of unwrapping the pack 11. In sealing the inner wrap unit 36 within the outer wrap 34, the open end of the outer wrap 34 is formed into a flap 41 and the flap 41 is folded back and sealed, for example, by using strips of adhesive tape 40 or by heat sealing or by any other sealing means, after insertion of the inner package unit 36. The inner package unit 36 is wrapped with a wrapping 60, constructed from commercially available gas permeable, sterile wrap, with water impermeable center strip such as KIM GUARD and the ends are folded back and sealed around the contents therein, for example by strips of adhesive tape 42. After unwrapping, wrapping 60 serves as a plastic disposable table cover and is generally of a size about 50"×90".

Figure 6:
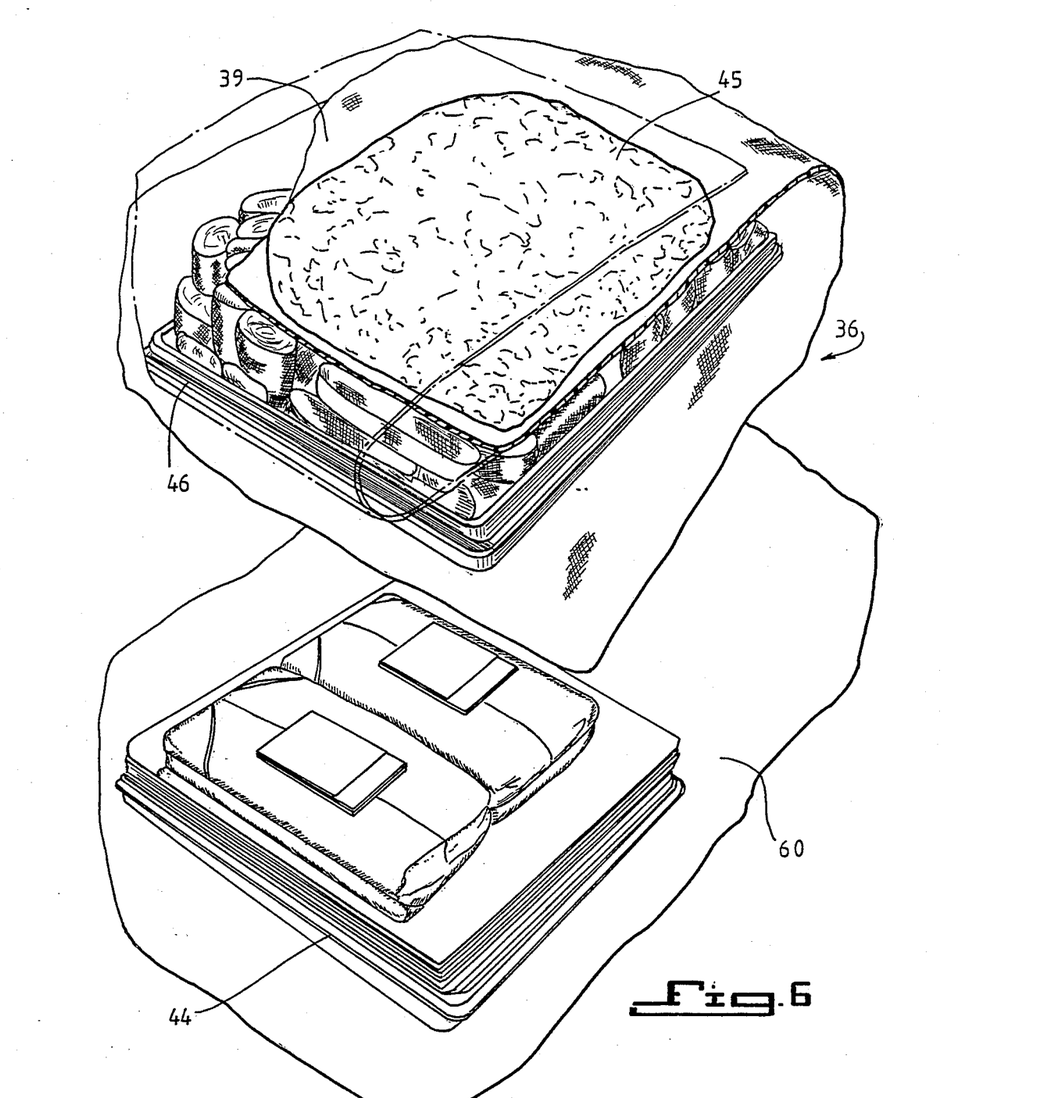
FIG. 6 is a perspective view of the unwrapped inner package unit of FIG. 5, showing some of the items contained therein.
Figure 6A:
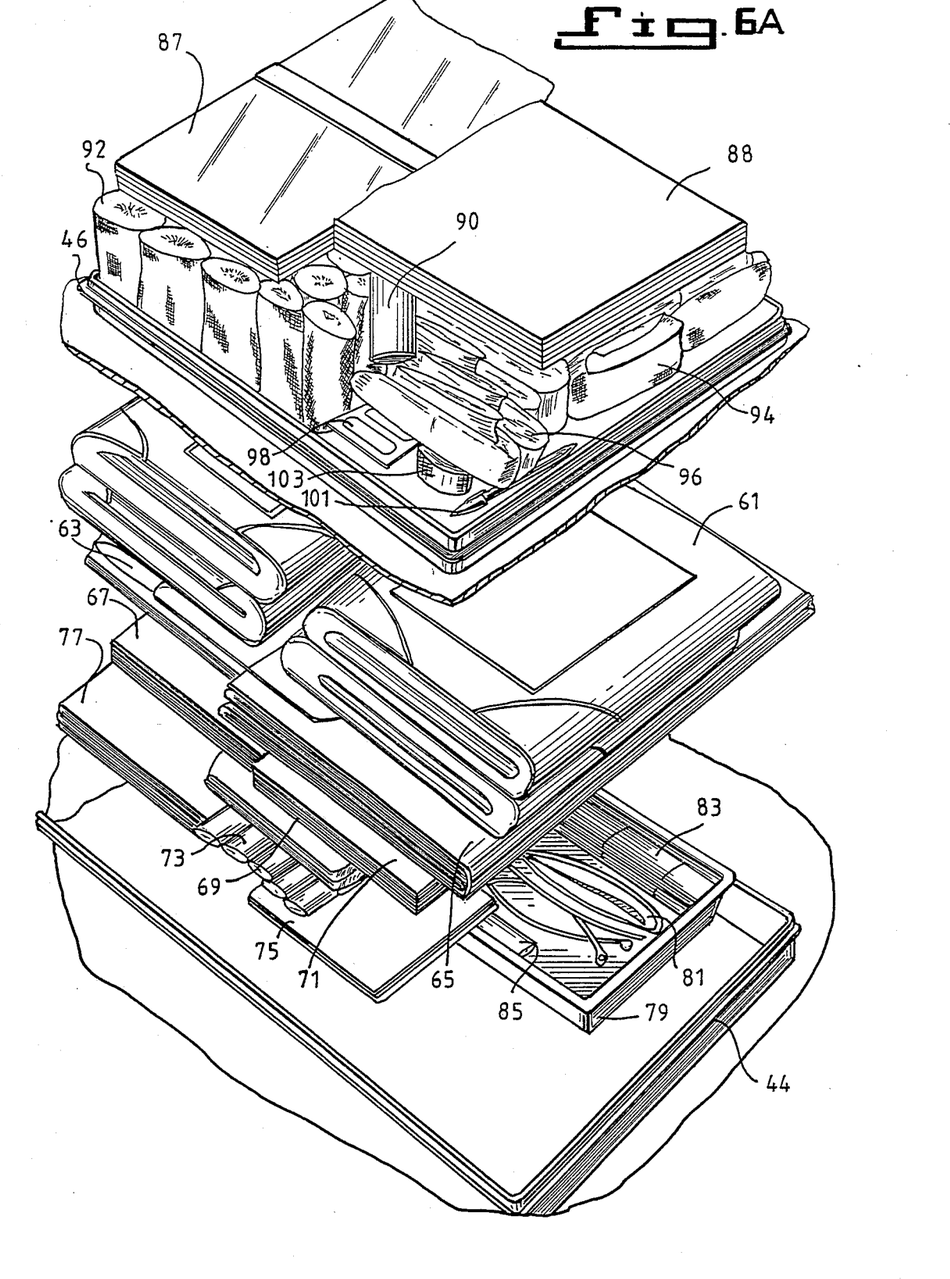
FIG. 6A is an exploded view of FIG. 6 showing the items contained in the inner package unit and the order of arrangement therein.

As illustrated in FIG. 6, the inner package unit 36 is comprised of a first tray 44 such as for example one of a size of about 14"×15"×1½", made from molded or thermo-formed sterilizable plastic and containing the following items arranged therein in the order of use. Thus, the items contained in tray 44, as better illustrated in FIG. 6A, from top to bottom are:

large disposable paper gown with towel 61, (preferably four in quantity), plastic disposable stand cover (Mayo Stand Cover) 63, (preferably one in quantity), disposable paper drape sheet (Drape Sheet 57"×77") 65, (preferably one in quantity), plastic split sheet with adhesive split and groin towel (Bilateral Split Sheet with Groin Towel) 67, (preferably one in quantity), plastic adherent split sheet (Plastic U Drape) 60"×70" with 20" adhesive split) 69, (preferably one in quantity), disposable paper drape (Utility Drape with Tape, 14"×26") 71, (preferably to in quantity), packaged clear plastic drapes (Steri Drapes (2045) (23¼"×17 ⅝", sticky portion 19⅝"×17 ⅜") 73, (preferably four in quantity), clear plastic drape (Incise Drape (1051) (35⅜"×33 ¾", sticky portion 23½×33⅜") 75, (preferably one in quantity), disposable paper drape (Drape with Tape (JOA)) 77, (preferably two in quantity), and contained in a separate plastic tray 79, said tray may be of a size of about 8½"×5"×1", are wire saw blades (Gigli Saw blades 20") 81, (preferably four in quantity), packaged surgical stainless steel blades (Blades #10) 83, (preferably 20 in quantity), and suture material 85 (preferably 10 in quantity).

As illustrated in FIG. 6 the inner package unit 36 contains a second tray 46, for example of a size of about 14"×15"×1½", which holds the following items in the order recited (better illustrated in FIG. 6A):

plastic bags (Plastic Bags 6"×18") 87, (preferably 48 in quantity), low particulating surgical sponges (Nu Gauze) 88, (preferably 55 in quantity), packaged clear plastic drape (Steri Drape (2040)), 14 ⅞"×16⅜", sticky portion 11"×16⅜") 90, (preferably one in quantity), stockinette (3"×22") 92, (illustrated in FIGS. 7 and 8) (preferably 36 in quantity), stockinette (6"×10") double thickness, sewn on one end 94, (illustrated in FIGS. 7 and 8) (preferably six in quantity), stockinette (3"×8") 96, (illustrated in FIGS. 7 and 8) (preferably 10 in quantity), labels 98, (preferably 60 in quantity), marking pens 101, (preferably two in quantity), and rayon taffete tape (silk)(Dermicel Tape 1"×10 yd.) 103, (preferably two rolls).

Tray 46 and its contents are wrapped in a wrapping 39 constructed from gas permeable with water impermeable center strip. Upon unwrapping, wrapping 39 serves as disposable table cover (with paper center cover e.g., a size of about 44"×84"). Wrapped tray 46 and its contents are placed over tray 44 and its contents and the stacked trays 44 and 46 and their respective contents are wrapped in inner wrapping 60 and sealed, as shown in FIG. 5. A folded table cover 45 (generally 50"×90") is separately wrapped over the contents of tray 46 by employing wrapping 39, as shown by FIG. 6. That is, one end of wrapping 39 is laid over the contents of tray 46, folded- table cover 45 is placed on top of this end of wrapping 39 and then the remaining end of wrapping 39 is laid over the table cover 45.

The order in which the afore-recited items are arranged as placed in trays 44 and 46 are essential to the present invention. That is, the items are arranged in each tray to provide the surgeon, technician or other assistant, ready access to all the required items without fumbling and/or loss of sterile conditions. Generally the items are placed in the trays in the opposite order of use, those used last are placed first and those used first are placed last.

In accordance with another embodiment of the present invention, a packaging means for transporting and storing the surgically removed bone and connective tissue, as well as a process for packaging and storing the removed bone and connective tissue, is provided.

Figure 7:
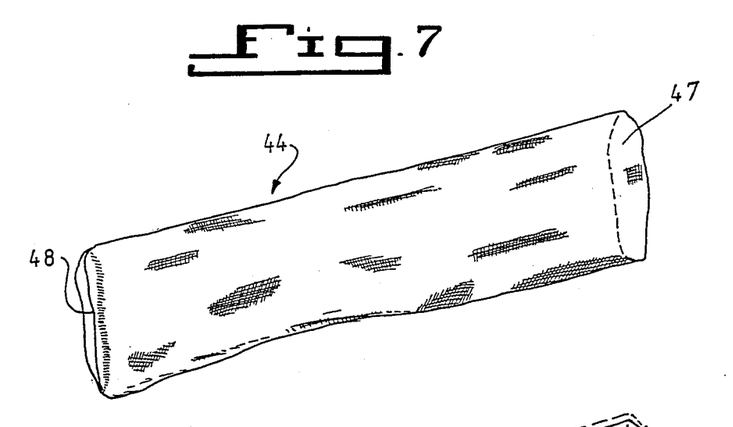
FIG. 7 is a perspective view of the packaging means in accordance with the present invention for packaging and storing bone and connective tissue.
Figure 8:
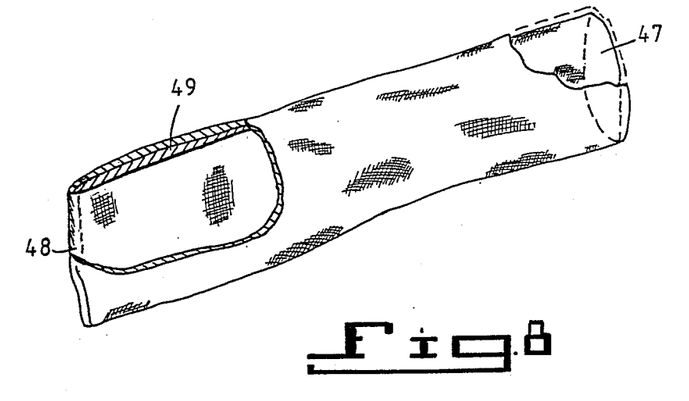
FIG. 8 is an inside out view of the packaging means of FIG. 7.

Referring more particularly to FIGS. 7 and 8, the packaging and storing means 44, for bone and connective tissue, of the present invention comprises a tubular woven material having an open end 47 and a sewn closed end 48.

Preferably, for the purposes of the present invention the tubular woven material from which the packaging means 44 is made known as stockinette and is readily commercially available. For the purposes of the present invention, and in order to provide a suitable packaging and storing receptacle for bone and connective tissue, stockinette, which is commercially available as open ended tubular material, is sewn closed at one end, as illustrated in FIGS. 7 and 8. A preferred form of the packaging means 44 of the present invention is illustrated in FIG. 8 wherein the packaging means is shown as being formed from with a double thickness of tubular woven material (depicted by numeral 49, and closed at end 48 by sewing said end closed. The packaging means 44 of the present invention may be of any size sufficient to contain a desired bone and connective tissue sample.

In still a further embodiment of the present invention, a process is provided for packaging and storing surgically removed bone and connective tissue. The process of the present invention provides for the storing of bone and connective tissue for extended periods of time (at the appropriate temperatures) whereby the bone and connective tissue remains in suitable condition for subsequent implantation in needy recipients.

Figures 9, 10, 11, 12, 13, 14:
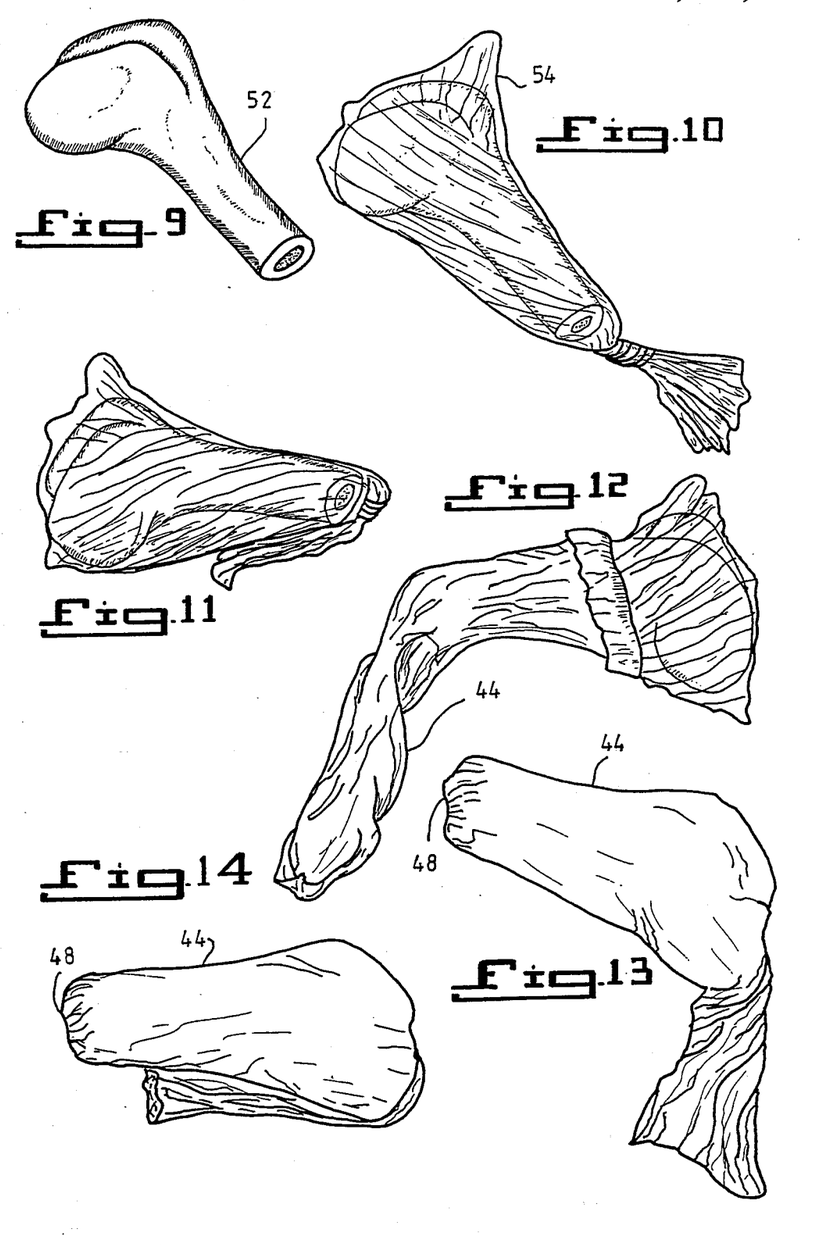
FIGS. 9 to 19, in sequence, illustrate in flow diagram fashion the process of the present invention for packaging bone and connective tissue, employing the packaging means of FIG. 7.
Figure 15:
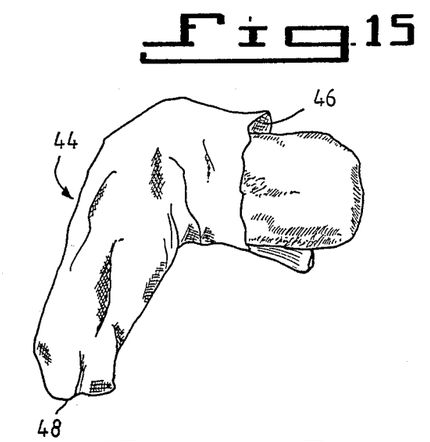
Figure 16:
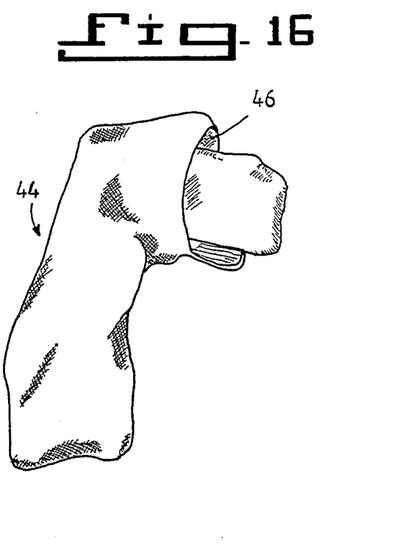

Thus, in accordance with this embodiment of the present invention and particularly referring to FIGS. 9 to 19 in sequence, the present process is carried out, for example, by placing, for example, the distal end of a left distal femur 52, after removal from a donor, into a plastic bag 54 (e.g., 6"×18") and twisting closed the open end of the plastic bag as shown in FIG. 10. After the plastic bag is twisted closed, the twisted end is folded under from the proximal to distal end of the femur, as shown in FIG. 11. Next, the twisted end of the plastic bag, containing the bone to be stored, is inserted in the open end of the packaging means 44 of the present invention constructed from stockinette and the bone is slid completely into the package means 44, as illustrated by FIGS. 12 and 13. At this stage of the process, the open end of packaging means 44 is folded longitudinally down the metaphyseal/diaphyseal shaft of the femur, as shown in FIG. 14. The packaged bone is then inserted (folded back end first) into a second packaging means 44, being certain that the bone seats itself at the closed end of the packaging means 44 as shown in FIG. 15. The open end of packaging means 44 is folded over again along the long axis of the bone and inserted (folded back end first) into a third packaging means 44, as shown in FIG. 16.

Figure 17:
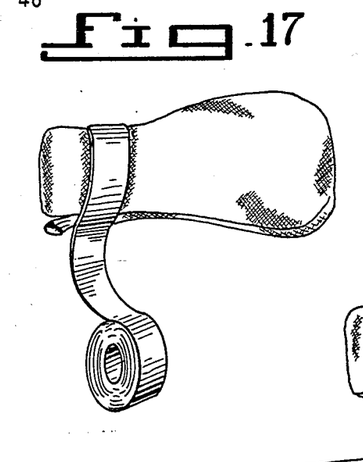
Figure 18:
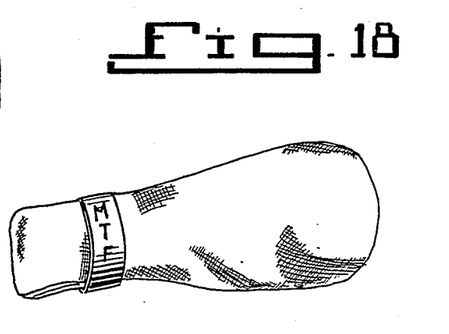

After the bone is inserted into the third packaging means 44, the open end is again folded longitudinally down the shaft of the bone and adhesive tape is circumferentially placed around the proximal end of the tissue, as illustrated in FIG. 17. The tape is then marked with the appropriate Musculoskeletal Transplant Foundation identification number and tissue identification code as shown in FIG. 18.

Figure 19:
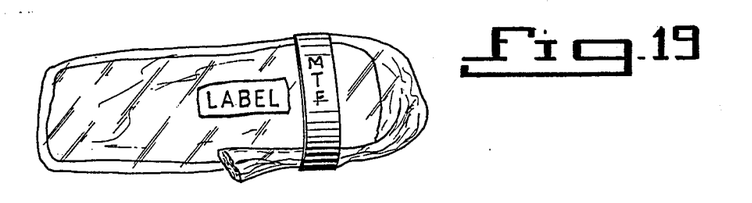

Finally, the bone and connective tissue is placed in an outer plastic bag, the open end is twisted, folded under as shown in FIG. 19 and the plastic bag is re-taped around the folded end and labelled, as shown in FIG. 19. The specimen is now ready for transport and storage.

While several embodiments and variations of the present invention have been described in detail herein, it is to be understood that various modifications may be made by those skilled in the art without departing from the spirit and scope of the present invention.

What is claimed is:

1. A medical and surgical procedure pack comprising in combination (i) a sealed, pre-sterilized outer wrap containing therein (ii) a sealed, wrapped, pre-sterilized inner package unit having contained therein the essential items necessary for surgically draping a donor to provide a sterile field prior to the surgical removal of bone and connective tissue therefrom and the essential items necessary for the surgical removal and packaging of said bone and connective tissue from said donor, said essential items necessary for the surgical removal and packaging of said bone and connective tissue including packaging means for said bone and connective tissue said packaging means comprising a woven material in a flexible tubular form, said flexible tubular form having an open end and a closed end.

2. The medical and surgical procedure pack of claim 1 wherein said outer wrap is constructed from an initially open ended bag, wherein said open end is formed into a flap and said flap is folded back and sealed.

3. The medical and surgical procedure pack of claim 1 wherein said outer wrap is constructed from an initially open ended bag having two heat pre-sealed sides and one pre-sealed tear-away side, wherein said open end is formed into a flap and said flap is folded back and sealed.

4. The medical and surgical procedure pack of claim 1 wherein said inner package unit is comprised of a first tray and a second tray, said first tray being stacked on top of said second tray and wherein said second tray contains all of the essential items necessary to drape a donor to provide a sterile field for the surgical removal of bone and connective tissue therefrom and said first tray contains all of the essential items necessary to surgically remove and package said bone and connective tissue including packaging means for said bone and connective tissue, said packaging means comprising a woven material in a flexible tubular form, said flexible tubular form having an open end and a closed end.

5. The medical and surgical procedure pack of claim 3 wherein said essential items in said first and second trays are arranged to allow for ready access so as to prevent the loss of sterilized conditions.

6. The medical and surgical procedure pack of claim 1 wherein said inner package unit is wrapped with wrapping constructed from a gas permeable material and wherein the ends of said wrapping are formed into flaps and wherein said flaps are sealed.

7. A medical and surgical procedure pack kit containing:
 (a) a first medical and procedure pack comprising in combination
  (i) a sealed, pre-sterilized outer wrap containing therein
  (ii) a sealed, wrapped, pre-sterilized inner package unit comprising a container having contained therein the essential items necessary for the preparation of a donor prior to the surgical removal of bone and connective tissue therefrom, said essential items arranged in said container to allow ready access of each item without the loss of sterilized conditions, said essential items comprising disposable absorbent towels, latex gloves, patient covering means, sponge sticks impregnated with antiseptic, scrub brushes impregnated with antiseptic, razors, soap sponge and spray bottle, wherein said outer wrap is constructed from an initially open ended bag constructed from a clear plastic material having two heat pre-sealed sides and one pre-sealed tear-away side, wherein said open end is formed into a flap and said flap is folded back and sealed and wherein said inner wrap unit is wrapped with wrapping constructed from a gas permeable material wherein the ends of said wrapping are folded back and sealed; and
 (b) a second medical and procedure pack comprising in combination
  (i) a sealed, pre-sterilized outer wrap containing therein
  (ii) a sealed, wrapped, pre-sterilized inner package unit having contained therein the essential items necessary for surgically draping a donor to provide a sterile field prior to the surgical removal of bone and connective tissue therefrom and the essential items necessary for the surgical removal and packaging of said bone and connective tissue from said donor, said essential items necessary for the surgical removal and packaging of said bone and connective tissue including packaging means for said bone and connective tissue, said packaging means comprising a woven material in a flexible tubular form, said flexible tubular form having an open end and a closed end.

* * * * *

UNITED STATES PATENT AND TRADEMARK OFFICE
CERTIFICATE OF CORRECTION

PATENT NO. : 4,844,259

DATED : July 4, 1989

INVENTOR(S) : Frank P. Glowczewski, Jr. and David A. Present

It is certified that error appears in the above-identified patent and that said Letters Patent is hereby corrected as shown below:

Column 4, line 51, "to" should read -- two --; and

Column 5, line 22, after "permeable", insert -- sterile wrap --.

Signed and Sealed this

Third Day of April, 1990

Attest:

HARRY F. MANBECK, JR.

*Attesting Officer*  *Commissioner of Patents and Trademarks*